United States Patent
Adams

(10) Patent No.: US 9,526,751 B2
(45) Date of Patent: Dec. 27, 2016

(54) CESIUM ELIMINATOR

(71) Applicant: Webseed, Inc., Cody, WY (US)

(72) Inventor: Michael A. Adams, Tuscon, AZ (US)

(73) Assignee: WEBSEED, INC., Cody, WY (US)

( * ) Notice: Subject to any disclaimer, the term of this patent is extended or adjusted under 35 U.S.C. 154(b) by 0 days.

(21) Appl. No.: 14/667,763

(22) Filed: Mar. 25, 2015

(65) Prior Publication Data

US 2015/0273001 A1     Oct. 1, 2015

Related U.S. Application Data

(60) Provisional application No. 61/973,597, filed on Apr. 1, 2014.

(51) Int. Cl.
| | | |
|---|---|---|
| *A61K 35/748* | (2015.01) | |
| *A61K 36/02* | (2006.01) | |
| *A61K 36/05* | (2006.01) | |
| *A61K 33/06* | (2006.01) | |
| *A61K 35/08* | (2015.01) | |

(52) U.S. Cl.
CPC ............. *A61K 35/748* (2013.01); *A23L 17/60* (2016.08); *A23L 29/015* (2016.08); *A23P 10/30* (2016.08); *A61K 33/06* (2013.01); *A61K 35/08* (2013.01); *A61K 36/05* (2013.01)

(58) Field of Classification Search
CPC ...... A61K 35/08; A61K 33/06; A61K 35/748; A61K 36/05; A61K 2300/00; A23L 1/0305; A23L 1/0029
See application file for complete search history.

(56) References Cited

U.S. PATENT DOCUMENTS

| | | | | |
|---|---|---|---|---|
| 4,192,756 A | * | 3/1980 | Mondshine | C01D 3/26 252/383 |
| 2007/0082008 A1 | * | 4/2007 | Harel | A23K 1/007 424/195.16 |

FOREIGN PATENT DOCUMENTS

| | | | | |
|---|---|---|---|---|
| CN | 102018135 A | * | 4/2011 | |
| PH | WO 2005032268 A2 | * | 4/2005 | ........... A23K 1/1612 |

OTHER PUBLICATIONS

Translation of CN 102018135A from Google. Translated on Feb. 8, 2016.*

* cited by examiner

*Primary Examiner* — Anoop Singh
*Assistant Examiner* — Doan Phan
(74) *Attorney, Agent, or Firm* — Neifeld IP Law, PC

(57) ABSTRACT

A dietary supplement comprising powdered ingredients: zeolite powder: 70%-5%, dehydrated seaweed: 5%-25%, seawater extract: 5%-10% *Chlorella*: 5%-10% and *Spirulina*: 5%-10%, methods of making and using the composition.

18 Claims, No Drawings

CESIUM ELIMINATOR

CROSS REFERENCE TO RELATED APPLICATIONS

This application claims benefit of Application No. 61/973/597, filed Apr. 1, 2014. The contents of Application No. 61/973/597 are hereby incorporated by reference in their entirety.

FIELD OF THE INVENTION

A dietary supplement having affinity for cesium-137 and cesium-134 (radioisotopes).

BACKGROUND OF THE INVENTION

Cesium Eliminator (CE-137) is a dietary supplement comprising zeolite powder plus four natural ingredients generally recognized as safe ("GRAS") by the FDA. In combination, they have the property of demonstrating strong affinity for cesium-137 and cesium-134.

CE-137 is a dietary supplement made of natural ingredients and assembled for the purpose of allowing people to consume the capsules alongside herbs, foods or beverages which they believe may contain radioactive cesium isotopes. Radioactive cesium mimics potassium in plant biology and is the primary long-term pollutant found in areas impacted by nuclear accidents such as Chernobyl and Fukushima. The half-life of cesium-137 is approximately 30 years. The isotope persists in an agricultural environment for 200-300 years with sufficient strength to make all foods grown in such soils too dangerous for consumption by humans or animals.

CE-137 is intended to be take orally during a meal in which components of the meal are suspected of containing concerning concentrations of cesium-134 or cesium-137. CE-137 selectively binds with the radioactive cesium isotopes, capturing them and removing them from the body through normal bowel movements that eliminate fecal matter. The primary benefit is that CE-137 prevents the radioisotopes from being absorbed through intestinal walls and into the bloodstream, thereby limiting the time the radioisotopes exist in the body.

SUMMARY OF THE INVENTION

An object of the invention is to provide a dietary supplement composition, comprising: powdered ingredients:
  a) Zeolite powder: 70%-95 wt. %
  b) Dehydrated seaweed: 5%-25 wt. %
  c) Seawater extract: 5%-10 wt. %
  d) *Chlorella:* 5%-10 wt. %
  e) *Spirulina:* 5%-10 wt. %
      particle sizes for all particles can be from #40 mesh to #100 mesh.

Another object of the invention is to provide a method of producing a dietary supplement composition, comprising combining powdered ingredients as follows,
  a) Zeolite powder: 70%-95 wt. %
  b) Dehydrated seaweed: 5%-25 wt. %
  c) Seawater extract: 5%-10 wt. %
  d) *Chlorella:* 5%-10 wt. %
  e) *Spirulina:* 5%-10 wt. %
      particle sizes for all particles can be from #40 mesh to #100 mesh.

Another object is to provide a method of causing cesium-137 and cesium-134 to be excreted from an animal, comprising feeding to an animal in need of fecal excretion of cesium-137 or cesium-134 a dietary supplement containing an effective amount of zeolite powder, wherein about 99% of particles in said zeolite powder are larger than 5 microns, plus effective amounts of dehydrated seaweed, seawater extract, *Chlorella*, and *Spirulina* to remove ionic aluminum or lead introduced by the zeolite.

DETAILED DESCRIPTION OF THE INVENTION

CE-137 is based on five key ingredients: zeolite powder, dehydrated seaweed, seawater extract, *chlorella, spirulina*. CE-137 is laboratory validated to bind with 96% of cesium atoms during digestion. The zeolite powder is the key element in this formula, as it binds with and captures cesium atoms.

However, zeolite powders normally release very high levels of aluminum, and somewhat high levels of lead. The other ingredients in the present invention are designed to bind with and capture the excess aluminum and lead that is introduced by the zeolites, allowing zeolites to be safely used to bind cesium.

Zeolites are, in general, microporous, aluminosilicate minerals of type Clinoptilolite. All zeolite materials contain a high concentration of aluminum in its structure. All zeolites also contain lead. Typically, zeolites which are digested in gastric acid release significant concentrations of aluminum, and much lower concentrations of lead. This invention makes use of chemistry discoveries and methods which minimize these releases of aluminum and lead, resulting in them being measured at near-zero levels.

It is believed that CE-137 works on a combination of physical adsorption as well as ion exchange. Without being bound by theory, it is thought that the zeolite physically adsorbs cesium atoms due to its unique physical structure. This adsorption process works in the same way that carbon (charcoal) adsorbs mercury. That is, it is a physical binding process, not necessarily a chemical ion exchange.

The aluminum and lead given off by zeolites are bound and captured by the other ingredients in the formula. It is thought that the Al and Pb are bound using ion exchange processes.

The finished CE-137 product is provided as an encapsulated powder. The powder is generally grayish white in color.

CE-137 is a dietary supplement comprising zeolites of size from #50 mesh to #100 mesh, plus natural ingredients assembled for the purpose of allowing people to consume the capsules alongside herbs, foods or beverages which they believe may contain cesium isotopes. CE-137 binds to cesium ions and prevents them from being absorbed through intestinal walls during digestion. Most dietary substances show little or no selective affinity for cesium when subjected to an identical testing process.

During digestion the gastric acid found in human stomachs interacts with CE-137 ingredients, causing them to attain a high state of affinity for ionic heavy metals such as lead and aluminum, Heavy metals tend to carry positive charges such as Aluminum (+3), Lead (+2), etc. CE-137 carries a strong negative ionic charge, once activated, causing it to bind with lead and aluminum.

The formula of the invention bind with and carries cesium isotopes plus the heavy metals introduced with the zeolites through the entire digestive tract, ultimately transporting the heavy metals out of the body and preventing them from being reabsorbed through intestinal walls.

Radiation Defense Ingredients Preparation

The following section describes the harvesting and preparation of each ingredient in the formula:

Zeolite powder (Clinoptilolite powder) is obtained by mining zeolite material from zeolite-rich mines which are located in North America and other nations such as Turkey. Raw zeolite material is scooped out of the ground using excavation equipment such as a Caterpillar 20-ton excavator. The material is loaded into large trucks which transport it to a washing station to remove dust and soil debris. Once washed, the material is dried and then milled to the desired mesh size.

Dehydrated seaweed: Seaweed specimens are collected by swimmers from shallow coastal waters and stacked in a large washing container. They are washed to remove debris and salt water. After washing they are dried using a large commercial air dryer with a slow mixing/agitation wheel in order to allow the seaweed sufficient exposure to air. Once fully dried, the seaweed specimens are ground to a power of approximately a #100 mesh size, producing a gray-white powder. This powder is packaged for use in manufacturing.

Seawater extract: A saturated salt (brine) area of seawater is identified, usually at very low depth. The water is extracted by means of a long pump, then mixed with dolomitic limestone ($CaMg(Co_3)_2$) to precipitate solids. The mixture is heated to high temperature, driving off the carbon dioxide and leaving "calcined dolime," a seawater extract. This solid material is ground to approximately #100 mesh particle size.

*Chlorella*: Strains of the single-celled algae known as *Chlorella vulgaris* are grown in large vats of water and fed sufficient nutrients to support their growth to maturity. Once fully grown, *chlorella* is harvested out of the water by means of large filters which separate the *chlorella* alga from the water in which they were grown. This green mass is rinsed with fresh water, flash dried on a conveyor belt, then agitated by powerful sonic blasts in order to disrupt their cell walls and provide improved bioavailability. Finally, this green mass is powdered to a relatively large mesh size of around #40 mesh.

*Spirulina*: *Spirulina pacifica* is a strain of edible blue-green algae which can be grown in large outdoor pools which combine fresh water with deep ocean water that enriches the *spirulina* with minerals. Once fully grown, the *spirulina* is harvested from the water by means of large filters giving a green mass which is rinsed with fresh water, flash dried on a conveyor belt, then ground to a relatively large mesh size of around #40 mesh.

Particle sizes of the above ingredient are specifically chosen to avoid passing through intestinal walls (99% of particles are >5 microns in diameter).

Carriers and processing aids may be used to obtain satisfactory flow and packaging characteristics. These excipients can include antitacking agents such as talc, stearic acid, magnesium stearate and colloidal silicon dioxide and the like, surfactants such as polysorbates and potassium lauryl sulphate, fillers such as precipitated calcium carbonate, polishing agents such as beeswax and the like. All these excipients can be used at levels well known to the persons skilled in the art In general the product is manufactured in an environment free of airborne metals in order to preserve the ion exchange "potential" of the raw materials.

In another embodiment, zeolite powder can be consumed separately, along with dehydrated seaweed: 5%-25%, Seawater extract: 5%-10%, *Chlorella*: 5%-10%, *Spirulina*: 5%-10%, with the Zeolite powder again constituting 70%-95%.

Laboratory Protocol for Validation of CE-137

CE-137 is specifically designed to minimize the release of aluminum and lead which are both typically released by zeolites. A typical off-the-shelf zeolite, when 3 grams are combined with 20 ml of synthetic gastric acid, will release approximately 8 mg of aluminum and 40 micrograms of lead. CE-137 reduces the release of these metals to approximately 20 micrograms of aluminum (or almost ⅕₀₀th the typical release) and near-zero micrograms of lead.

The following protocol is used for laboratory validation of the CE-137 formula:

First, all laboratory protocols for handling radioactive substances must be followed, including operating air exchange filters, wearing protective lead vests, wearing protective lead-based goggles and wearing respirators with filters that can capture and remove airborne radioactive dust.

In addition, radiological samples must be acquired through legal processes requiring registration and licensing with the Nuclear Regulatory Commission (NRC). All safety protocols and laboratory procedures customarily used for handling radioactive materials must be strictly followed.

One gram of CE-137 formula is placed in a polypropylene vial (vial #1). A second vial is set aside for control testing (vial #2), with no CE-137 placed in it (zero grams).

To each vial, 20 ml of synthetic gastric acid is added. This acid has a pH of around 1.0 and is made of deionized water (DI), hydrochloric acid (HCl), sodium chloride and potassium chloride, all in ratios that mimic typical human gastric acid.

A 2 ml liquid "spike" of radioisotope Cs-137 is then added to both vials using precise volumetric liquid handling via pipette. This spike contains a known concentration of Cs-137, typically in the range of 5 ppm-15 ppm. The strength of the radiation given off by the Cs-137 is not relevant, only the concentration of cesium atoms.

Both vials are then subjected to simulated digestion for a period of 8 hours. This digestion consists of human body temperature and agitation designed to mimic digestion in the human stomach.

After digestion, both vials are filtered through a 2-micron filter to remove any solid particles which would be too large to pass through intestinal walls. 5 ml of the remaining liquid is extracted from each vial and placed in a fresh, new vial in preparation for acid digestion. 5 ml of nitric acid ($HNO_3$) is added to each vial. Both vials are digested via HotBlock digestion, at a temperature of 100° C. for a period of two hours. The vials are then removed from the HotBlock and allowed to cool.

Both vials are then normalized to 50 ml total volume using a blank acid normalization liquid made of DI water, 2% $HNO_3$ and 0.5% HCl. These vials are placed in an autosampler connected to an ICP-MS atomic spectroscopy instrument which has been calibrated by the manufacturer and validated by field technicians.

The instrument runs a multi-element custom calibration process followed by a mid-range calibration check. Calibration blanks are also run before and after the samples in order to further confirm the accuracy of the instrument. External calibration solutions are prepared and rm at 0 ppb, 1 ppb, 10 ppb, 100 ppb and 1000 ppb concentrations. And internal standard is mixed with the sample intake liquid for analysis accuracy.

Unknown samples are then run and concentrations of analytes are calculated from the calibration runs, as it customary in all ICP-MS laboratory operations. Specifically, analytes tested in this protocol must include Cs, Al and Pb. The cesium concentration found in vial #2 provide the "baseline concentration" of cesium atoms in the total 22 ml of synthetic gastric acid. Cesium concentrations found in vial #1 are then compared to the baseline. The difference in the two concentrations is the reduction of cesium-137 concentration caused by the CE-137 formula.

In addition, Al and Pb concentrations found in vial #1 are compared to zero, which is the level of Al and Pb in the gastric acid. All Al and Pb found in vial #1 are known to have been released by the CE-137 formula, which is specifically designed to substantially minimize these releases.

In this laboratory testing. CE-137 was shown to accomplish approximately a 96% reduction in Cesium-137. In addition, the introduction of aluminum and lead, both typically released by zeolite materials, are minimized essentially to zero due to the ion exchange effects of the accompanying materials in the CE-137 formula; resulting in Al below 1 ppm, and resulting in Pb below 50 ppb.

Most dietary substances, when subjected to an identical testing process show little or no selective affinity for cesium-137 binding.

Encapsulation Process

The CE-137 powder is encapsulated and packaged using traditional powder encapsulation methods which are customarily used in dietary supplements manufacturing. Specifically, raw materials are weighed, apportioned and blended using a large commercial blender. The resulting blended power is deposited into the encapsulation machine. Empty vegetarian capsules are also deposited into the machine. The machine opens each capsule and fills each capsule with approximately 400 mg of power, then firmly closes each capsule.

Capsules are then counted by machine and dropped into supplement bottles. Desiccants are dropped into the bottles to absorb moisture. A capper affixes a cap with a special seal containing both a sealant and a thin metallic element which is sensitive to induction. An induction machine exposes the lid of the bottle to a brief electric current sufficient to create heat to seal the top of the bottle, under the lid. A shrink bander machine affixes a shrink band around the neck of the bottle. A heat tunnel shrinks the shrink band, creating a tight seal. A labeler affixes the product label. The bottle is then boxed into cases for distribution.

It will be apparent to those skilled in the art that variations and modifications of the invention can be made without departing from the spirit and scope of the teachings above. It is intended that the specification and examples be considered as exemplary only and are not restrictive.

The invention claimed is:

1. A dietary supplement composition, consisting of:
Powdered ingredients encapsulated in a water-soluble vegetable capsule and consisting of:
a) Zeolite powder: #50 mesh, 70 wt. %
b) Dehydrated seaweed particles: #100 mesh, 5 wt. %
c) Calcined dolime particles, as seawater extract: #60 mesh, 5% -10 wt. %
d) *Chlorella vulgaris* particles: #40 mesh, 5% -10 wt. %
e) *Spirulina pacifica* particles: #40 mesh, 5% -10 wt. % and
f) a remainder of excipient particles selected from the group consisting of anticaking agent, surfactant, filler, and polishing agent; wherein the anticaking agent is talc, stearic acid, magnesium stearate or colloidal silicon dioxide; wherein the surfactant is polysorbate or potassium lauryl sulfate; wherein the filler is precipitated calcium carbonate; wherein the polishing agent is beeswax;
wherein 99% of all particles in the composition are larger than 5 microns in diameter.

2. A method of producing the dietary supplement composition, of claim 1, consisting of:
combining the powdered ingredients, and encapsulating in the capsule, to produce the composition.

3. The method of claim 2, wherein the composition is produced in an environment free of airborne heavy metals.

4. A method of causing cesium isotopes to be excreted from an animal, consisting of:
feeding to an animal in need of fecal excretion of cesium isotopes the composition of claim 1.

5. The composition of claim 1, wherein the calcined dolime particles are 5 wt. %.

6. The composition of claim 1, wherein the calcined dolime particles are 10 wt. %.

7. The composition of claim 1, wherein the *Chlorella vulgaris* particles are 5 wt. %.

8. The composition of claim 1, wherein the *Chlorella vulgaris* particles are 10 wt. %.

9. The composition of claim 1, wherein the *Spirulina pacifica* particles are 5 wt. %.

10. The composition of claim 1, wherein the *Spirulina pacifica* particles are 10 wt. %.

11. The composition of claim 1, wherein the excipient particles are anticaking agent.

12. The composition of claim 11, wherein the anticaking agent is talc.

13. The composition of claim 11, wherein the anticaking agent is stearic acid.

14. The composition of claim 11, wherein the anticaking agent is magnesium stearate.

15. The composition of claim 11, wherein the anticaking agent is colloidal silicon dioxide.

16. The composition of claim 1, wherein the excipient particles are surfactant.

17. The composition of claim 16, wherein the surfactant is polysorbate.

18. The composition of claim 16, wherein the surfactant is potassium lauryl sulfate.

* * * * *